United States Patent
Yang

(10) Patent No.: US 7,456,314 B2
(45) Date of Patent: Nov. 25, 2008

(54) PARTIALLY FLUORINATED IONIC COMPOUNDS

(75) Inventor: Zhen-Yu Yang, deceased, late of Hockessin DE (US); by Amy Qi Han, legal representative, Hockessin, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/955,508

(22) Filed: Dec. 13, 2007

(65) Prior Publication Data

US 2008/0161612 A1 Jul. 3, 2008

Related U.S. Application Data

(60) Provisional application No. 60/876,315, filed on Dec. 21, 2006.

(51) Int. Cl.
 *C07C 315/00* (2006.01)
(52) U.S. Cl. .................................................. 564/35
(58) Field of Classification Search ............ 568/35
 See application file for complete search history.

(56) References Cited

U.S. PATENT DOCUMENTS

| 3,282,875 | A | | 11/1966 | Connolly et al. |
| 3,664,915 | A | | 5/1972 | Gore |
| 3,953,566 | A | | 4/1976 | Gore |
| 3,962,153 | A | | 6/1976 | Gore |
| 4,187,390 | A | | 2/1980 | Gore |
| 4,358,545 | A | | 11/1982 | Ezzell et al. |
| 5,547,551 | A | | 8/1996 | Bahar et al. |
| 6,002,055 | A | * | 12/1999 | Yang .......................... 570/142 |
| 6,100,324 | A | * | 8/2000 | Choi et al. .................. 524/493 |
| 6,107,422 | A | * | 8/2000 | Wang et al. .................. 526/243 |
| 6,110,333 | A | | 8/2000 | Spethmann et al. |
| 6,214,955 | B1 | * | 4/2001 | Yang .......................... 526/252 |
| 6,255,543 | B1 | * | 7/2001 | Yang .......................... 570/135 |
| 6,265,507 | B1 | * | 7/2001 | Wang et al. .................. 526/253 |
| 6,268,430 | B1 | * | 7/2001 | Choi et al. .................. 524/544 |
| 6,294,289 | B1 | | 9/2001 | Fanta et al. |
| 6,667,377 | B2 | | 12/2003 | Feiring et al. |

OTHER PUBLICATIONS

Y. Sone et al., "Proton Conductivity of Nafion® 117 As Measured by a Four-Electrode AC Impedance Method", Journal of the Electrochemical Society, Aprl. 1996, pp. 1254-1259, vol. 143 (4).

* cited by examiner

*Primary Examiner*—Yvonne Eyler
*Assistant Examiner*—Chukwuma O Nwaonicha

(57) ABSTRACT

Partially fluorinated ionic compounds are prepared. They are useful in the preparation of partially fluorinated dienes, in which the repeat units are cycloaliphatic.

5 Claims, No Drawings

PARTIALLY FLUORINATED IONIC COMPOUNDS

FIELD OF THE INVENTION

Disclosed are partially fluorinated ionic compounds, useful in the preparation of partially fluorinated dienes, in which the repeat units are cycloaliphatic. This invention was made with government support under Contract No. DE-FC04-02AL67606 awarded by the U.S. Department of Energy. The government has certain rights in the invention.

BACKGROUND

It has long been known in the art to form ionically conducting polymer electrolyte membranes and gels from organic polymers containing ionic pendant groups. Well-known so-called ionomer membranes in widespread commercial use are Nafion® perfluoroionomer membranes available from E.I. du Pont de Nemours and Company, Wilmington Del. Nafion® is formed by copolymerizing tetrafluoroethylene (TFE) with perfluoro(3,6-dioxa-4-methyl-7-octenesulfonyl fluoride), as disclosed in U.S. Pat. No. 3,282,875. Other well-known perfluoroionomer membranes are copolymers of TFE with perfluoro(3-oxa-4-pentene sulfonyl fluoride), as disclosed in U.S. Pat. No. 4,358,545. The copolymers so formed are converted to the ionomeric form by hydrolysis, typically by exposure to an appropriate aqueous base, as disclosed in U.S. Pat. No. 3,282,875. Lithium, sodium and potassium are all well known in the art as suitable cations for the above cited ionomers.

Low equivalent weight is necessary to obtain high conductivity, but this could cause poor mechanical properties. One approach to solve these problem is to make new cyclic polymers which usually have high glass transition temperature ("Tg") and good mechanical properties.

Free radical polymerizations which include nonconjugated dienes (and bis vinyl ethers) usually yield polymers which are crosslinked because of the "separate" reaction of each of the double bonds with the free radicals in the reactions. However, it is known that in some instances perfluorinated or partially fluorinated compounds containing two such double bonds do not form crosslinked polymers, but form polymers containing cyclic structures.

In U.S. Pat. Nos. 6,214,955 and 6,255,543 selected partially fluorinated monomers and the corresponding polymers were prepared. However, these polymers were not made into films and also did not contain any ionomeric substituents.

What is needed, therefore, are new cyclic, fluorinated monomers and polymers that can be formed into conductive films with good mechanical properties.

SUMMARY

Disclosed is a composition of Formula (II)

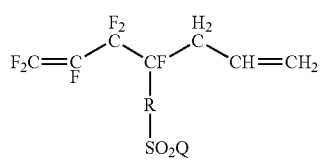

(II)

wherein R comprises a linear or branched perfluoroalkene group of 1 to 20 carbon atoms, optionally containing oxygen or chlorine; Q is chosen from F, —OM, —NH$_2$, —NHCN, —N(M)SO$_2$R$^2$, —N(CN)SO$_2$R$^2$, —C(M)(CN)$_2$, —C(M)(CN)(SO$_2$R$^2$) and —C(M)(SO$_2$R$^2$)$_2$; R$^2$ is an optionally fluorinated 1 to 14 carbon alkyl group, optionally containing ether oxygen linkages, or an optionally fluorinated 6-12 carbon aryl group; and M is independently H, an alkali cation, ammonium or substituted ammonium.

Also disclosed is a composition of Formula (III)

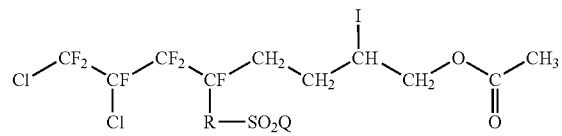

(III)

and a composition of Formula (IVA)

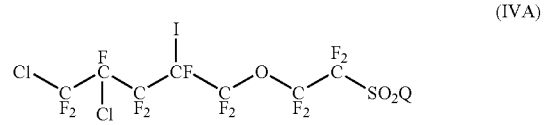

(IVA)

wherein R, Q, R$^2$ and M are as defined above.

DETAILED DESCRIPTION

Disclosed herein are polymers that are useful as cation-exchange resins. The cation-exchange resins are useful in making proton-exchange membranes for electrochemical cells such as fuel cells and can be used in any application wherein cation-exchange capacity is desired. The resins may also be used as electrolytes, electrode binders, sensors, electrolysis cells, in lithium batteries in lithium salt form, and in any application requiring charge-transfer phenomena, such as components of light-emitting displays. The polymers described herein can be either homopolymers or copolymers.

Described herein is a polymer comprising one or more of the repeat units (IA), (IB) or (IC):

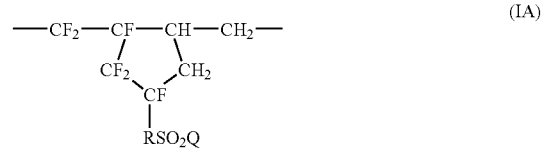

(IA)

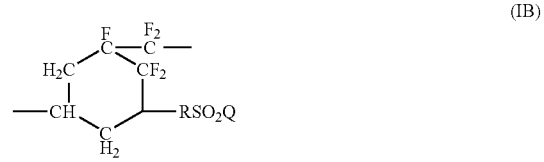

(IB)

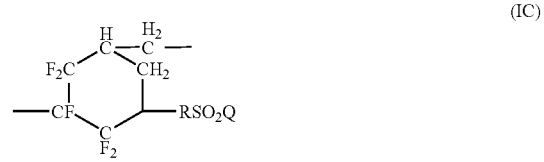

(IC)

wherein R comprises a linear or branched perfluoroalkylene group of 1 to 20 carbon atoms, optionally containing oxygen or chlorine;

Q is chosen from F, —OM, —NH$_2$, —NHCN, —N(M)SO$_2$R$^2$, —N(CN)SO$_2$R$^2$, —C(M)(CN)$_2$, —C(M)(CN)(SO$_2$R$^2$) and —C(M)(SO$_2$R$^2$)$_2$;

R$^2$ is an optionally fluorinated 1 to 14 carbon alkyl group, optionally containing ether oxygen linkages, or an optionally fluorinated 6-12 carbon aryl group; and M is independently H, an alkali cation, ammonium or substituted ammonium.

By "alkyl" it is meant a monovalent group containing only carbon and hydrogen, chiral or achiral, connected by single bonds and/or by ether linkages, and substituted accordingly with hydrogen atoms. It can be linear, branched, or cyclic. By "alkylene" it is meant a divalent alkyl group.

By "optionally fluorinated" it is meant that one or more of the hydrogens can be replaced with fluorines.

By "perfluorinated alkylene" it is meant a divalent group containing carbon and fluorine connected by single bonds, optionally substituted with ether oxygens or other halogens, and containing two free valences to different carbon atoms.

The term "copolymer" is intended to include oligomers and copolymers having two or more different repeating units. A copolymer having repeating units derived from a first monomer "X-A-X" and a second monomer "X—B—X" will have repeating units (-A-) and (—B—). The copolymers described herein can be random or block copolymers.

The practical upper limit to the number of monomeric units in the polymer is determined in part by the desired solubility of a polymer in a particular solvent or class of solvents. As the total number of monomeric units increases, the molecular weight of the polymer increases. The increase in molecular weight is generally expected to result in a reduced solubility of the polymer in a particular solvent. Moreover, in one embodiment, the number of monomeric units at which a polymer becomes substantially insoluble in a given solvent is dependent in part upon the structure of the monomer. In one embodiment, the number of monomeric units at which a copolymer becomes substantially insoluble in a given solvent is dependent in part upon the ratio of the comonomers. For example, a polymer composed of flexible monomers may become substantially insoluble in an organic solvent if the resulting polymer becomes too rigid in the course of polymerization. As another example, a copolymer composed of several monomers may become substantially insoluble in an organic solvent when ratio of rigid monomeric units to flexible monomeric units is too large. The selection of polymer molecular weight, polymer and copolymer composition, and a solvent is within the purview of one skilled in the art.

The monovalent cation M can be a single cation or a mixture of different cations. In one embodiment, the M is K, Na, Li, or H. In another embodiment, Q is F, —OM, or —NH$_2$, and more typically F. In the case where Q is F, the polymer can easily be converted to other embodiments using means well known in the art. They can be hydrolyzed with bases such as MOH or M$_2$CO$_3$ in solvents such as methanol, DMSO and water. The hydrolysis is usually carried out at room temperature to 100° C., preferably at room temperature to 50° C. Treatment with acids such as HNO$_3$ will give polymers where Q is OM. Reaction with R$^2$SO$_2$NH$_2$ and triethylamine, and subsequent after hydrolysis with acid will give polymers where Q=NHSO$_2$R$^2$. Other methods known in the art can also be used, such as those disclosed in U.S. Pat. Nos. 6,667,377 and 6,294,289, herein incorporated by reference.

In one embodiment R is (CF$_2$)$_x$ where x=1 to 16, (CF$_2$)$_y$OCF$_2$CF$_2$ where y=1 to 12, or (CF$_2$CF(CF$_3$)O)$_z$CF$_2$CF$_2$ where z is 1 to 6, R$^2$ is methyl, ethyl, propyl, butyl, or phenyl, each of which may be partially fluorinated or perfluorinated. In another embodiment x=1 to 4, y=1 to 4, and z is 1 to 2, and R$^2$ is perfluoromethyl, perfluoroethyl, or perfluorophenyl.

In another embodiment, the polymer comprises one or more of the repeat units (IA'), (IB') or (IC'):

(IA')

(IB')

(IC')

wherein Q is as defined above but is typically F.

The polymers can be prepared via the free-radical polymerization of one or more compounds of Formula (II):

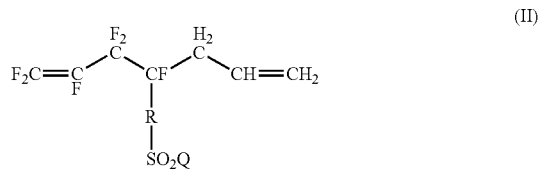
(II)

wherein R, Q, R$^2$, and M are as defined above. In one embodiment R is (CF$_2$)$_x$ where x=1 to 16, (CF$_2$)$_y$OCF$_2$CF$_2$ where y=1 to 12, or (CF$_2$CF(CF$_3$)O)$_z$CF$_2$CF$_2$ where z is 1 to 6, R$^2$ is methyl, ethyl, propyl, butyl, or phenyl, each of which may be partially fluorinated or perfluorinated. In another embodiment x=1 to 4, y=1 to 4, and z is 1 to 2, and R$^2$ is perfluoromethyl, perfluoroethyl, or perfluorophenyl. The monovalent cation M can be a single cation or a mixture of different cations. In one embodiment, the M is K, Na, Li, or H. In another embodiment, Q is F, —OM, or —NH$_2$.

Compounds of Formula (II) can be prepared via the reaction scheme outlined below:

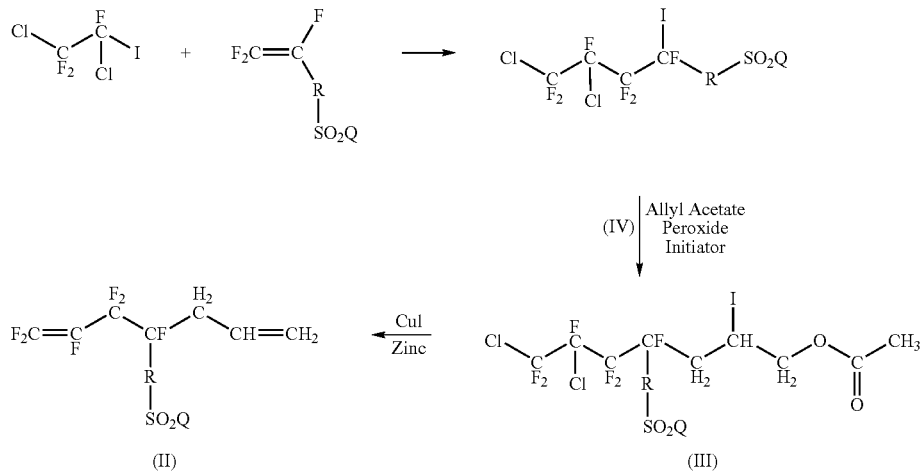

where R, Q, $R^2$, and M are as defined above. The reactions can be done in any suitable solvent or mixture of solvents, including the reactants themselves. Suitable solvents include but are not limited to N-methyl pyrrolidinone, dioxane, acetic acid, or alcohol. Any peroxide initiator can be used, such as but not limited to benzoyl peroxide or potassium peroxodisulfate. The products at each step can be purifed by any known means, such as but not limited to distillation or extraction.

The last step of the reaction is typically run under an inert atmosphere such as nitrogen. Other metals can be used in place of the Zn metal, such as but not limited to Mg.

In one embodiment, Formulae (II), (III) and (IV) are Formula (IIA), (IIIA), and (IVA) respectfully:

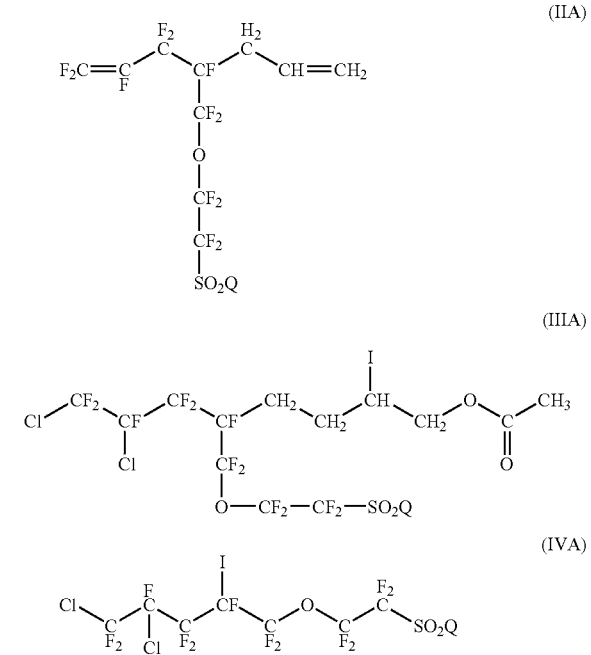

wherein Q is as defined above but is typically F.

The compounds of Formulae (II), (III) and (IV) are useful as monomers or comonomers for various polymers, including polymers comprising one or more of the repeat units (IA), (IB) or (IC).

Suitable comonomers include but are not limited to tetrafluoroethylene, hexafluoropropylene, vinylidene fluoride, perfluoro(methyl vinyl ether), perfluoro(propyl vinyl ether), methyl vinyl ether, propylene, ethylene, chlorotrifluoroethylene, perfluoro(2,2-dimethyl-1,3-dioxole), methyl vinyl ether, ethylene, and propylene. Any of these comonomers may be optionally substituted, such as substitution with one or more —$SO_2Q$ groups.

The polymerization of compounds of Formula (II) to form polymers comprising one or more of the repeat units (IA), (IB) or (IC) may be done neat, in aqueous emulsion or suspension, in solution or organic suspension. They may be done in batch, semibatch or continuous operations. A free radical polymerization initiator is typically used, such as but not limited to peroxides such as perfluoro(propionyl peroxide) (3P), azonitriles such as azobis(isobutylronitrile) (AIBN), and redox initiators such as persulfate-bisulfite. A surfactant can also be used, typically a partially fluorinated or perfluorinated surfactant. The surfactant can be anionic, cationic, or nonionic. Suitable surfactants include, are not limited to, sodium dodecylsulfate, alkyl benzene sulfonates, dextrins, alkyl-ether sulfonates, ammonium sulfates, Triton® surfactants, and fluorinated surfactants such as C8 (ammonium perfluorooctanoate) Zonyl® fluorosurfactants such as Zonyl® 62, Zonyl® TBS, Zonyl® FSP, Zonyl® FS-62, Zonyl® FSA, Zonyl® FSH, and fluorinated alkyl ammonium salts such as but not limited to $R'_w NH_{(4-w)}X$ wherein X is $Cl^-$, $Br^-$, $I^-$, $F^-$, $HSO_4^-$, or $H_2PO_4^-$, where w=4-4, where R' is ($R_F CH_2 CH_2$)—. Zonyl® fluorosurfactants are available from E. I. DuPont de Nemours, Wilmington, Del., and in general are anionic, cationic, amphoteric or nonionic oligomeric hydrocarbons containing ether linkages and fluorinated substituents.

The polymerizations can be performed at any temperature at which the reaction proceeds at a reasonable rate and does not lead to degradation of the product or catalyst. The process is generally run at a temperature at which the selected initiator generates free radicals. The reaction time is dependent upon the reaction temperature, the amount of catalyst and the concentration of the reactants, and is usually about 1 hour to about 100 hours.

The polymers can be recovered according to conventional techniques including filtration and precipitation using a non-solvent. They also can be dissolved or dispersed in a suitable solvent for further processing.

The polymers described herein can be formed into membranes using any conventional method such as but not limited to solution or dispersion film casting or extrusion techniques. The membrane thickness can be varied as desired for a particular application. Typically, for electrochemical uses, the membrane thickness is less than about 350 μm, more typically in the range of about 15 μm to about 175 μm. If desired, the membrane can be a laminate of two polymers such as two polymers having different equivalent weight. Such films can be made by laminating two membranes. Alternatively, one or both of the laminate components can be cast from solution or dispersion. When the membrane is a laminate, the chemical identities of the monomer units in the additional polymer can independently be the same as or different from the identities of the analogous monomer units of the first polymer. One of ordinary skill in the art will understand that membranes prepared from the dispersions may have utility in packaging, in non-electrochemical membrane applications, as an adhesive or other functional layer in a multi-layer film or sheet structure, and other classic applications for polymer films and sheets that are outside the field of electrochemistry. For the purposes of the present invention, the term "membrane", a term of art in common use in electrochemistry, is synonymous with the terms "film" or "sheet", which are terms of art in more general usage, but refer to the same articles.

The membrane may optionally include a porous support or reinforcement for the purposes of improving mechanical properties, for decreasing cost and/or other reasons. The porous support may be made from a wide range of materials, such as but not limited to non-woven or woven fabrics, using various weaves such as the plain weave, basket weave, leno weave, or others. The porous support may be made from glass, hydrocarbon polymers such as polyolefins, (e.g., polyethylene, polypropylene, polybutylene, and copolymers), and perhalogenated polymers such as polychlorotrifluoroethylene. Porous inorganic or ceramic materials may also be used. For resistance to thermal and chemical degradation, the support typically is made from a fluoropolymer, more typically a perfluoropolymer. For example, the perfluoropolymer of the porous support can be a microporous film of polytetrafluoroethylene (PTFE) or a copolymer of tetrafluoroethylene. Microporous PTFE films and sheeting are known that are suitable for use as a support layer. For example, U.S. Pat. No. 3,664,915 discloses uniaxially stretched film having at least 40% voids. U.S. Pat. Nos. 3,953,566, 3,962,153 and 4,187,390 disclose porous PTFE films having at least 70% voids. Impregnation of expanded PTFE (ePTFE) with perfluorinated sulfonic acid polymer is disclosed in U.S. Pat. Nos. 5,547,551 and 6,110,333. ePTFE is available under the trade name "Goretex" from W. L. Gore and Associates, Inc., Elkton, Md., and under the trade name "Tetratex" from Tetratec, Feasterville, Pa.

Membrane electrode assemblies (MEA) and fuel cells therefrom are well known in the art and can comprise any of the membranes described above. One suitable embodiment is described herein. An ionomeric polymer membrane is used to form a MEA by combining it with a catalyst layer, comprising a catalyst such as platinum, which is unsupported or supported on carbon particles, a binder such as Nafion®, and a gas diffusion backing. The catalyst layers may be made from well-known electrically conductive, catalytically active particles or materials and may be made by methods well known in the art. The catalyst layer may be formed as a film of a polymer that serves as a binder for the catalyst particles. The binder polymer can be a hydrophobic polymer, a hydrophilic polymer, or a mixture of such polymers. The binder polymer is typically ionomeric and can be the same ionomer as in the membrane. A fuel cell is constructed from a single MEA or multiple MEAs stacked in series by further providing porous and electrically conductive anode and cathode gas diffusion backings, gaskets for sealing the edge of the MEA(s), which also provide an electrically insulating layer, graphite current collector blocks with flow fields for gas distribution, aluminum end blocks with tie rods to hold the fuel cell together, an anode inlet and outlet for fuel such as hydrogen, and a cathode gas inlet and outlet for oxidant such as air.

EXAMPLES

In-Plane Conductivity Measurement

The in-plane conductivity of membranes was measured under conditions of controlled relative humidity and temperature by a technique in which the current flowed parallel to the plane of the membrane. A four-electrode technique was used similar to that described in an article entitled "Proton Conductivity of Nafion® 117 As Measured by a Four-Electrode AC Impedance Method" by Y. Sone et al., J. Electrochem. Soc. 143, 1254 (1996) that is herein incorporated by reference. A lower fixture was machined from annealed glass-fiber reinforced Poly Ether Ether Ketone (PEEK) to have four parallel ridges containing grooves that supported and held four 0.25 mm diameter platinum wire electrodes. The distance between the two outer electrodes was 25 mm, while the distance between the two inner electrodes was 10 mm. A strip of membrane was cut to a width between 10 and 15 mm and a length sufficient to cover and extend slightly beyond the outer electrodes, and placed on top of the platinum electrodes. An upper fixture which had ridges corresponding in position to those of the bottom fixture, was placed on top and the two fixtures were clamped together so as to push the membrane into contact with the platinum electrodes. The fixture containing the membrane was placed inside a small pressure vessel (pressure filter housing), which was placed inside a forced-convection thermostated oven for heating. The temperature within the vessel was measured by means of a thermocouple. Water was fed from a calibrated Waters 515 HPLC pump (Waters Corporation, Milford, Mass.) and combined with dry air fed from a calibrated mass flow controller (200 sccm maximum) to evaporate the water within a coil of 1.6 mm diameter stainless steel tubing inside the oven. The resulting humidified air was fed into the inlet of the pressure vessel. The total pressure within the vessel (100 to 345 kPa) was adjusted by means of a pressure-control letdown valve on the outlet and measured using a capacitance manometer (Model 280E, Setra Systems, Inc., Boxborough, Mass.). The relative humidity was calculated assuming ideal gas behavior using tables of the vapor pressure of liquid water as a function of temperature, the gas composition from the two flow rates, the vessel temperature, and the total pressure. The slots in the lower and upper parts of the fixture allowed access of humidified air to the membrane for rapid equilibration with water vapor. Current was applied between the outer two electrodes while the resultant voltage was measured between the inner two electrodes. The real part of the AC impedance (resistance) between the inner two electrodes, R, was measured at a frequency of 1 kHz using a potentiostat/frequency response analyzer (PC4/750™ with EIS software, Gamry Instruments, Warminster, Pa.). The conductivity, κ, of the membrane was then calculated as $$\kappa = 1.00 \text{ cm}/(R \times t \times w),$$

where t was the thickness of the membrane and w was its width (both in cm).

EXAMPLES

Example 1

Preparation of $CF_2ClCFClCF_2CFlCF_2OCF_2CF_2SO_2F$

A mixture of 167 g $CF_2ClCFlCl$ and 130 g of $CF_2=CFCF_2OCF_2CF_2SO_2F$ was heated at 200° C. in an autoclave for 30 hrs. Distillation gave fractions at bp 26° C./250 mmHg to 27° C./25 mmHg, 114 g, and bp 57° C./0.08 mmHg to 61/0.06 mmHg, 144.5 g. The product was then distilled via spinning band to give 109.2 g of pure product, bp 83° C./2.3 mmHg. NMR analysis: $^{19}F$ NMR: +45.70 (m, 1F), −62.5 (m, 0.5F), −63.6 (m, 1.5 F), −71.8 to −73.5 (m, 1F), −75.6 to −76.7 (m, 1F), −82.6 (s, 2F), −96.8 to −101.5 (m, 1.5F), −105.0 to −106.0 (m, 0.5F). −112.4 (m, 2F), −125.5 (m, 0.5 F), −129.0 (m, 0.5F), −138.8 (m, 0.5F), −142.6 (m, 0.5F). IR: 1465 (s, $SO_2F$), 1271 to 1121 (vs, C-F) cm$^{-1}$. Analysis: Calculated for $C_7F_{13}Cl_2SO_3I$: C, 13.81; F, 40.56; Cl, 11.64; I, 20.84; S, 5.27. Found: C, 13.76; F, 42.06; Cl, 11.25; I, 20.82; S, 5.12.

Example 2

Preparation of $AcOCH_2CHICH_2CF(CF_2CFClCF_2Cl)$ $CF_2OCF_2CF_2SO_2F$

To a stirred mixture of 5.0 g (0.05 mol) of allyl acetate and 30.4 g (0.05 mol) of $CF_2ClCFClCF_2CFlCF_2OCF_2CF_2SO_2F$ from Example 1 was added 0.2 g of benzoyl peroxide at 85° C. in $N_2$. An exothermic reaction occurred and the temperature increased to 120° C. After cooling to 110° C., an additional 0.1 g of benzoyl peroxide was added and the reaction mixture was stirred for 30 min. 0.3 g of benzoyl peroxide was then added in a fraction of 0.2 g every 30 min. GC (gas chromatography) indicated no starting materials remained, and the mixture was evaporated at full vacuum to remove impurity to give 36.1 g (98%) of the pure adduct. NMR analysis: $^1H$ NMR: 4.6-4.1 (m, 3H), 3.2-2.8 (m, 2H), −2.1(m, 3H). $^{19}F$ NMR: +45.4 (m, 1F), −62.3 to −63.9 (m, 1.5F), −75.6 to −78.8 (m, 1.5F), −82.5 (m, 2F), −107.5 to −111.0 (m, 2F), −112.4 (m, 2F), −130.6 to −131.3 (m, 1F), −180.2 to −182.6 (m, 1F). IR: 1753 (s, $CH_3CO_2$), 1463 (s, $SO_2F$), −1216 to −1149 (vs, C-F) cm$^{-1}$. HRMS: Calculated for $C_{12}H_9O_5F_{13}SCl_2I$: 708.8385. Found: 708.8376.

Example 3

Preparation $CH_2=CHCH_2CF(CF_2CF=CF_2)$ $CF_2OCF_2CF_2SO_2F$

A 200 mL flask was charged with 9.8 g of Zn (0.15 mol), 1.0 g of CuI and 50 mL of N-methyl prrolidinone under $N_2$. Next, 33 g (0.45 mol) of $AcOCH_2CHICH_2CF(CFClCF_2Cl)$ $CF_2O CF_2CF_2SO_2F$ was added dropwise at room temperature. In order to keep the temperature below 30° C. during the addition the flask was cooled with cool water.

After the addition was complete, the reaction mixture was heated to 80° C. for 1 hr and then the condenser was replaced with a distillation head. All volatiles were distilled out in full vacuum and the receiver cooled with dry ice until half of mixture had distilled. The distillate was poured into water and the low layer was separated, washed with water and/or brine for several times. Finally, the crude product was distilled at 10 mmHg to give pure product, bp 58° C./1.5 mmHg. NMR analysis: $^{19}F$ NMR. −77.2 (dm, J=137.6 Hz, 1 F), −77.4 (dm, J=137.6 Hz, 1F). −82.4 (m, 2F), −90.8 (dt, J=38.1 Hz, J=6.0 Hz, 1F), −91.0 (dt, J=38.1 Hz, J=6.0 Hz, 1F), 106.1 (m, 1F), −112.6 (m, 2F), −180.2 (m, 1F), −186.0 (dm, J=116.8 Hz, 1F). $^1H$ NMR: 5.95 (m, 1H), 5.20 (m, 2H), 2.80 (m, 2H). RHMS: Calcd for $C_{12}H_9O_3F_{12}S$ (M+$C_2H_5$–HF, The exact mass measurement was taken with the M+$C_2H_5$ peak): 461.0081. Found: 461.0061.

Example 4

Polymerization of $CH_2=CHCH_2CF(CF_2CF=CF_2)$ $CF_2OCF_2CF_2SO_2F$

A three necked clean flask fitted with a condenser top with a $N_2$ inlet/outlet, a stirring bar and a thermal meter was charged with 15 mL of deionized water and 1 mL of 20% ammonium perfluorooctanoate solution. The solution was bubbled with $N_2$ for 30 min. 2.0 g of $CH_2=CHCH_2CF$ $(CF_2CF=CF_2)CF_2O CF_2CF_2SO_2F$ was added to the flask via a syringe under $N_2$ and ultrasonically mixed to make an emulsion solution. After heating to 80° C., 0.5 mL of solution (made from 24 mg of potassium peroxodisulfate in 1 mL of deionized water) was added via a syringe and the flask was kept at 80° C. for 2 hrs. (It was very important to maintain the temperature at 80° C.). An additional 0.5 mL of initiator solution was added and stirred for another 2 hrs. The flask was cooled with dry ice until frozen, then was warmed up to room temperature. After 5 ml of 20% $HNO_3$ was added in order to coagulate the polymer, the mixture was stirred at 90 for 30 min, cooled to room temperature, filtered and washed with water for 3 times to give a white powder. The powder was dried in a vacuum oven at 100° C. for 4 hrs to give 1.8 g of polymer. DSC (differential scanning calorimetry) indicated that the polymer had a $T_m$ of 55° C. at first heat and $T_g$ of 52° C. at second heat. By TGA (thermal gravimetric analysis), 5% weight loss of polymer was 330° C. in air when heated at 10° C./min. IR indicated no double bond absorption. $^1H$ NMR ($CF_3Ph$): 2.30 to 3.5 (m). $^{19}F$ NMR: +42.5 (s,1F), −81.2 to −84.7 (m, 2F), −85.2 (m, 2F), −105.0 to −113.1 (m, 2F), −115.0 (s, 2F), −119.8 (m) and −122.8 (m) total 2F. −159.2 to −161 (m), −170 (m), −175.7 to −179.0 (m) and −190.1 (m) total 2F. Analysis: calculated for $C_{10}H_5F_{13}SO_3$: C, 26.55; H, 1.11; F, 54.64; S, 7.07. Found: C, 26.83; H, 1.05; F, 54.68; S, 7.07.

Example 5

Polymerization of $CH_2=CHCH_2CF(CF_2CF=CF_2)$ $CF_2O CF_2CF_2SO_2F$ in F113

A glass tube was charged with 10 mg of Percadox 16N, (bis-4-t-butyl-cyclohexyl)peroxydicarbonate, Akzo Nobel Polymer Chemicals LLC Chicago, Ill.) 6 mL of 1,2,2-trichlorotrifluoroethane and 1.0 g of $CH_2=CHCH_2CF$ $(CF_2CF=CF_2)CF_2OCF_2CF_2SO_2F$. After being cooled at −78° C., the tube was evacuated and purged with $N_2$ for 5 times and then sealed. The sealed tube was heated at 65° C. for 20 hrs. The resulting viscous liquid was poured into hexane. Solid polymer was isolated and dried overnight in a vacuum oven at 100° C. DSC indicated polymer had a $T_m$ of 55° C. at first heat and a $T_g$ of 52° C. at second heat. By TGA, 5% weight loss of polymer was 330° C. in air when heated at 10° C./min. $^1$H NMR (CF$_3$Ph): 2.30 to 3.5 (m). $^{19}$F NMR: +42.5 (s,1F), −81.2 to −84.7 (m, 2F), −85.2 (m, 2F), −105.0 to −113.1 (m, 2F), −115.0 (s, 2F), −119.8 (m) and −122.8 (m) total 2F. −159.2 to −161 (m), −170 (m), −175.7 to −179.0 (m) and −190.1 (m) total 2F. Analysis: Calcd for $C_{10}H_5F_{13}SO_3$: C, 26.55; H, 1.11; F. 54.64; S, 7.07. Found: C, 26.58; H, 0.72; F, 53.82; S, 7.31.

Example 6

Preparation of Membrane 1.3 g of the polymer prepared in Example 2 was suspended in 10% (NH$_4$)$_2$CO$_3$ in 1 to 1 methanol and water solution at 50° C. for 2 days. After removal of volatiles, the residue was dried in a 110° C. vacuum oven overnight and then treated with concentrated HCl at 50° C. for 6 hrs. 1.1 g of solids were obtained by filtration and dried at 100° C. in a vacuum oven overnight. Polymer was dissolved in methanol, coated onto expanded PTFE (poly-tetrafluoroethylene) film and dried first in air and then at 60° C. in vacuum oven. The conductivity of the sample was measure in-plane at 120° C. under controlled humidity varying from 25% first to 95% at the end. The conductivity values are shown below:

| RH % | Conductivity (mS/cm) |
|---|---|
| 25 | 16.6 |
| 50 | 45.3 |
| 95 | 274.1 |

What is claimed is:

1. A composition of Formula (II)

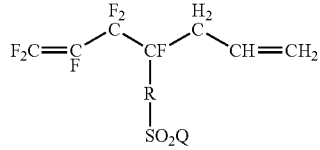

(II)

wherein R comprises a linear or branched perfluoroalkene group of 1 to 20 carbon atoms, optionally containing oxygen or chlorine;

Q is chosen from F, —OM, —NH$_2$, —NHCN, —N(M)SO$_2$R$^2$, —N(CN)SO$_2$R$^2$, —C(M)(CN)$_2$, —C(M)(CN)(SO$_2$R$^2$) and —C(M)(SO$_2$R$^2$)$_2$;

R$^2$ is an optionally fluorinated 1 to 14 carbon alkyl group, optionally containing ether oxygen linkages, or an optionally fluorinated 6-12 carbon aryl group; and M is independently H, an alkali cation, ammonium or substituted ammonium.

2. The composition of claim 1 wherein R is (CF$_2$)$_x$ where x=1 to 16, (CF$_2$)$_y$OCF$_2$CF$_2$ where y=1 to 12, or (CF$_2$CF(CF$_3$)O)$_z$CF$_2$CF$_2$ where z is 1 to 6; and wherein R$^2$ is methyl, ethyl, propyl, butyl, or phenyl, each of which may be partially fluorinated or perfluorinated.

3. The composition of claim 2 where x=1 to 4, y=1 to 4, and z is 1 to 2; and R$^2$ is perfluoromethyl, perfluoroethyl, or perfluorophenyl.

4. The composition of claim 1 wherein Q is F.

5. The composition of claim 1 wherein Formula (II) is Formula (IIA)

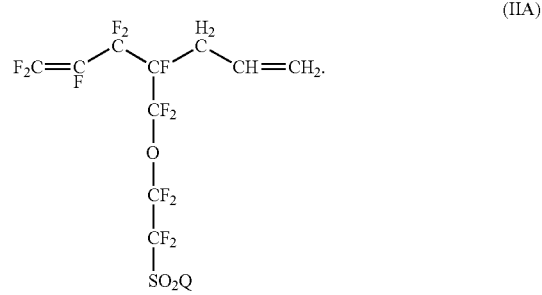

(IIA)

* * * * *